United States Patent
Marshall et al.

(10) Patent No.: US 6,410,579 B2
(45) Date of Patent: Jun. 25, 2002

(54) USE OF PRAMIPEXOLE FOR THE TREATMENT OF ADDICTIVE DISORDERS

(75) Inventors: Robert Clyde Marshall, Mattawan; Erik Ho Fong Wong, Portage; Philip F. Von Voigtlander, Plainwell, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/783,656

(22) Filed: Feb. 14, 2001

Related U.S. Application Data

(60) Provisional application No. 60/184,242, filed on Feb. 23, 2000.

(51) Int. Cl.[7] .................................. A61K 31/425
(52) U.S. Cl. .................. 514/367; 514/439; 514/443
(58) Field of Search .................. 514/439, 443, 514/367

(56) References Cited

U.S. PATENT DOCUMENTS

| | | | |
|---|---|---|---|
| 4,886,812 A | 12/1989 | Griss et al. | 514/321 |
| 5,112,842 A | 5/1992 | Zierenberg et al. | 514/367 |
| 6,001,861 A | 12/1999 | Oertel | 514/367 |

FOREIGN PATENT DOCUMENTS

| | | |
|---|---|---|
| DE | 38 43 227 | 12/1988 |
| DE | 39 33 738 | 10/1989 |
| EP | 0186087 | 12/1985 |
| EP | 0417 637 A | 3/1991 |
| EP | WO94/13287 | 6/1994 |
| WO | WO96/18395 | 6/1996 |
| WO | WO 0122820 | 4/2001 |

OTHER PUBLICATIONS

S. Caine, et al. "D3–receptor test in vitro predicts decreased cocain self–administration in rats", XP002168920 & NeuroReport (1997), 8(9–10), 2373–2377 abstract.

A.Carlsson and M.F.Piercey, "Dopamine–Receptor Subtypes in Neurological and Psychiatric Disease", Clinical Neuropharmacology, 1995, vol. 18, Suppl. 1, pp S1–S5.

H.D.Kleber, "Pharmacotherapy, Current and Potential, for the Treatment of Cocaine Dependence", Clinical Neuropharmacology, 1995, vol. 18, Suppl. 1, pp S96–S109.

Ma J J, et al. "The Behavioral Effects of Pramipexole, A Novel Dopamine Receptor Agonist", European Journal of Pharmacology, 1997, vol. 324, No. 1, pp. 31–37.

D.C.S. Roberts and R. Ranaldi, "Effect of Dopaminergic Drugs on cocaine Reinforcement", Clinical Neuropharmacology, 1995, vol. 18, Suppl. 1, pp. S84–S95.

R.A. Wise, "D1– and D2–Type Contributions to Psychomoter Sensitization and Reward: Implications for Pharmacological Treatment Strategies", Clinical Neuropharmacology, 1995, vol. 18, Suppl. 1, pp S74–S83.

*Primary Examiner*—Dwayne C. Jones
*Assistant Examiner*—C. Delacroix-Muirheid
(74) *Attorney, Agent, or Firm*—Austin W. Zhang; Thomas A. Wootton

(57) ABSTRACT

This patent application describes the treatment addictive disorders, psychoactive substance use disorders, intoxication disorders, inhalation disorders, alcohol addiction, tobacco addiction and or nicotine addiction comprising administering a therapeutically effective, nontoxic dose of pramipexole and derivatives and or pharmaceutically acceptable salts thereof to a patient.

14 Claims, No Drawings

USE OF PRAMIPEXOLE FOR THE TREATMENT OF ADDICTIVE DISORDERS

CROSS-REFERENCE TO RELATED APPLICATIONS

This application claims the benefit of the following provisional application: U.S. Ser. No. 60/184,242, filed Feb. 23, 2000 under 35 USC 119(e)(i).

FIELD OF THE INVENTION

The present invention relates to the use of pramipexole or 2-amino-6-n-propylamino-4,5,6,7-tetrahydrobenzo-thiazole or the (−)-enantiomers thereof, and the pharmacologically acceptable salts thereof, for the treatment of several nervous system disorders, including: Addictive Disorders, Psychoactive Substance Use Disorders, Nicotine Addiction or Tobacco Addiction resulting in Smoking Cessation.

BACKGROUND OF THE INVENTION

Pramipexole is a dopamine-$D_3/D_2$ agonist the synthesis of which is described in European Patent 186 087 and its counterpart, U.S. Pat. No. 4,886,812. It is known primarily for the treatment of schizophrenia and Parkinson's disease. German patent application DE 38 43 227 suggests pramipexole lowers the plasma level of prolactin. The English abstract of this case states that among the numerous pituitary gland related disorders that may be treated with pramipexole, it might be useful to treat illnesses caused by DA receptor blockage or DA secretion inhibition caused by medicaments. Further, it is known from German patent application DE 39 33 738 that pramipexole can be used to decrease abnormal high levels of thyroid stimulating hormone (TSH). U.S. Pat. No. 5,112,842 discloses the transdermal administration of the compounds and transdermal systems containing these active compounds. The WO patent application PCT/EP 93/03389 describes pramipexole as an antidepressant agent. PCT application PCT/US95/15618 discloses neuroprotective effects of pramipexole. U.S. Pat. No. 5,001,861 describes the use of pramipexole for the treatment of Restless Legs Syndrome.

Scientists have also considered whether drugs like pramipexole might have useful properties to treat some forms of addiction. For example, see, A Carlsson, MF Piercey, Dopamine Receptor Subtypes in Neurological Psychiatric Diseases, *Clinical Neuropharmacology*, Vol. 18, Suppl. I, pp. S1–S5 (1995). R A Wise, D1- and D2-Type Contributions to Psychomotor Sensitization and Reward: Implications for Pharmacological Treatment Strategies, *Clinical Neuropharmacology*, Vol. 18, Suppl. I, pp. S-74–83 (1995). D C S Roberts, R Ranaldi, Effect of Dopaminergic Drugs on Cocaine Reinforcement, *Clinical Neuropharmacology*, Vol. 18, Suppl. I, pp. S84–S95 (1995). H D Kleber, Pharmacotherapy, Current and Potential, for the Treatment of Cocaine Dependence, *Clinical Neuropharmacology*, Vol. 18, Suppl. I, pp. S96–S109 (1995).

Here we disclose methods and dosages that explain how pramipexole can be used to treat specific addictive disorders.

SUMMARY OF THE INVENTION

The present invention particularly provides a method for the treatment of certain addictive disorders, such as pychoactive substance use disorders, nicotine addiction or tobacco addiction (with a result of smoking cessation or a decrease in smoking) comprising administering a therapeutically effective, nontoxic dose of pramipexole and derivatives and or pharmaceutically acceptable salts thereof to a patient suffering from or susceptible to such an addiction or disorder comprising the administration of an effective amount of pramipexole. By pramipexole is meant 2-amino-6-n-propylamino-4,5,6,7-tetrahydrobenzothiazole, its (−)-enantiomer thereof, or (S)-2-amino-4,5,6,7-tetrahydro-6-(propylamino)-benzothiazole and pharmacologically acceptable salts thereof especially (−)-2-amino-6-n-propylamino-4,5,6,7-tetrahydrobenzothiazole dihydrochloride ($H_2O$).

2-Amino-6-n-propyl-amino-4,5,6,7-tetrahydrobenzothiazole, particularly the (−)-enantiomer thereof, and the pharmacologically acceptable acid addition salts thereof can be given for treating the addictive disorders described here. The form of conventional preparations consist essentially of an inert pharmaceutical carrier and an effective dose of the active substance; e.g., plain or coated tablets, capsules, lozenges, powders, solutions, suspensions, emulsions, syrups, suppositories, etc.

Preferred are tablets containing the following amounts of active drug, in mg/tablet: 0.125, 0.25, 0.5, 1.0, 1.25 and 1.5 mg of pramipexole base (mg pramipexole 2HCl), respectively, and further comprising mannitol, maize starch, colloidal silica, polividone and magnesium stearate as excipients. Preferred would be starting dose of 0.125 mg provided to a patient 3 times per day (tid). After accepting the starting dose, the patient may then seek to increase the dosage to a higher level with increases every 5 to 7 days up to a maximum dose of 10 mg/day, a preferred higher total daily dosage of about 6 mg/day with a more preferred highest dosage of about 4.5 to 5 mg/day.

For treating the addictive disorders described herein the drug may also be provided in chewable format, such as a chewing gum. The amount of active drug put in a chewable base may be half that suggested above, starting with about 0.075 mg per square of chewing gum being administered tid and followed with higher levels after the patient shows tolerance to the drug. Several chewing gum dosages are considered here including; 0.075, 0.10, 0.125, 0.150, in addition to those mentioned for a tablet. One or two chewing gum squares could be provided up to three times a day, depending on the therapeutic need of the patient.

Transdermal administration, such as with a skin patch application, and inhalation therapy, such as with an inhaler, is also foreseen where the patch or inhaler would deliver levels of pramipexole to the patient's blood in levels comparable to that suggested herein. A transdermal patch containing pramipexole could also be combined with a patch containing nicotine with the goal being the elimination of craving for tobacco containing products.

The drug is typically first administered to a patient at a low dosage to avoid possible nausea that may occur with higher starting doses. The dose is then titrated up to higher levels until a suitable therapeutic effect is acheived.

The effective dose range can be from 0.01 to 10.0 mg/day and patient, preferred is between 0.125 and 6 mg/day, more preferred between 0.375 to 5 mg/day and especially preferred is between 0.75 and 4.5 mg/day to a patient. In addition to being administered by oral or intravenous route pramipexole may also be administered transdermally or by inhalation.

Dosages should be typically increased gradually from a starting dose of about 0.125 mg of base drug given to the patient three times per day and then increased every 5–7 days until optimal therapeutic effect is achieved. Providing patients do not experience intolerable side effects, the dosage should be titrated to achieve a maximal therapeutic effect. One ordinarily skilled in art of providing medicine, such as a physician or pharmacist should be able to determine the optimal dosage level after considering a patients age, size, medical history, responsiveness to and toleration for the drug.

Description of the Disorders that May Be Treated With Pramipexole

Addictive disorders and psychoactive substance use disorders, such as intoxication disorders, inhalation disorders, alcohol addiction, tobacco addiction and/or nicotine addiction. Tobacco and nicotine addiction would be treated with the goal of achieving either smoking cessation or smoking reductions.

Addictive disorders, alcohol and other psychoactive substance use disorders, disorders related to intoxication and inhalants and especially tobacco addiction or nicotine addiction, may be treated with pramipexole. Tobacco addiction or nicotine addiction would be treated with pramipexole in order to achieve smoking/chewing cessation or smoking/chewing reduction. General descriptions of addictive disorders, including disorders related to intoxication and inhalants and tobacco addiction or nicotine addiction may be found in many standard sources, such as, The American Psychiatric Press Textbook of Psychiatry, Second Edition, Edited by Robert E. Hales, Stuart C. Yudofsky, and John A. Talbott, copyright 1994, incorporated by reference, especially pp. 401 et. seq., section on "Nicotine" incorporated by reference. Another of many texts is the Manual of Psychiatric Therapeutics, Second Edition, edited by Richard I. Shader, incorporated by reference, especially pp. 85 from Chapter 11 (Hypnosis).

The treatment of alcohol and other psychoactive substance use disorders, such as disorders related to intoxication and inhalants and tobacco addiction or nicotine addiction but especially tobacco addiction involves the administration of pramipexole in a manner and form that provide a reduction in the symptoms of the disease. Tobacco addiction or nicotine addiction in particular would be treated to achieve a reduction or cessation of smoking or chewing of nicotine containing materials by a patient. Cessation or a reduction in smoking or chewing of addictive or psychoactive substances involves the administration of pramipexole in a manner and form that provide a reduction in the symptoms of the disease, or with tobacco or nicotine with a reduction in the amount smoked or chewed. See the description above for methods and dosages for the proper administration of pramipexole for the treatment of these diseases and symptoms.

What is claimed is:

1. A method of treating or enhancing the treatment of a disorder selected from, addictive disorders, psychoactive substance use disorders, intoxication disorders, inhalation disorders, alcohol addiction, tobacco addiction and nicotine addiction comprising:

administering a therapeutically effective, nontoxic dose of a compound selected from the group consisting of pramipexole, an (−)-enantiomer of pramipexole, pramipexole dihydrochloride, pramipexole dihydrochloride-($H_2O$), and a pharmaceutically acceptable salt of any said compound to a patient, wherein said compound is administered orally or by inhalation.

2. The method of claim 1 where pramipexole is used to treat or enhance the treatment of Tobacco and or Nicotine Addiction.

3. The method of claim 2 where pramipexole is used to reduce the craving for Tobacco or Nicotine containing products.

4. The method of claim 2 where pramipexole is used to reduce the smoking or chewing of Tobacco or Nicotine containing products.

5. The method of claim 1 wherein the dose of pramipexole is about 0.01–10.0 mg/day.

6. The method of claim 5 wherein the dose of pramipexole is about 0.125–6 mg/day.

7. The method of claim 6 wherein the dose of pramipexole begins at 0.125 mg administered to the patient 3 times a day and is then titrated to higher levels every 5 to 7 days until therapeutic effect is achieved.

8. The method of claim 6 wherein the dose of pramipexole is about 0.375–5 mg/day.

9. The method of claim 8 wherein the dose of pramipexole is about 0.75–4.5 mg/day.

10. The method of claim 1 wherein the disorder is selected from the group consisting of inhalation disorders and alcohol addiction.

11. The method of claim 1 wherein the pramipexole or a pharmaceutically acceptable salt thereof is provided in a dosage form comprising tablet, chewable form, or inhaler.

12. The method of claim 11 wherein the pramipexole or a pharmaceutically acceptable salt thereof is provided in a dosage form of tablet and wherein the amount of pramipexole or a pharmaceutically acceptable salt thereof is from about 0.125 to about 1.5 mg per tablet.

13. The method of claim 11 wherein the pramipexole or a pharmaceutically acceptable salt thereof is provided in a chewable dosage form consisting of chewing gum.

14. The method of claim 13 wherein the amount of pramipexole or a pharmaceutically acceptable salt thereof is from about 0.075 to about 1.0 mg per square of chewing gum.

* * * * *